United States Patent [19]

Sarges et al.

[11] 4,248,882
[45] Feb. 3, 1981

[54] TREATING DIABETES-ASSOCIATED COMPLICATIONS WITH HYDANTOIN AMINES

[75] Inventors: Reinhard Sarges, Mystic; Rodney C. Schnur, Noank, both of Conn.

[73] Assignee: Pfizer Inc., New York, N.Y.

[21] Appl. No.: 120,944

[22] Filed: Feb. 12, 1980

[51] Int. Cl.³ .................. A61K 31/415; A61K 31/47; C07D 495/10; C07D 491/107
[52] U.S. Cl. ............................... 424/273 R; 424/258; 546/18; 548/309
[58] Field of Search ......................... 546/18; 548/309; 424/273 R, 258

[56] References Cited

U.S. PATENT DOCUMENTS

| 3,534,037 | 10/1970 | Loev | 546/18 X |
|---|---|---|---|
| 3,821,383 | 6/1974 | Sestanj et al. | 424/258 |
| 4,117,230 | 9/1978 | Sarges | 548/309 |
| 4,130,714 | 12/1978 | Sarges | 548/309 |
| 4,176,185 | 11/1979 | Schnur | 546/18 X |
| 4,177,282 | 12/1979 | Sarges | 424/273 R |
| 4,181,729 | 1/1980 | Sarges et al. | 548/309 X |

FOREIGN PATENT DOCUMENTS 1135915  9/1962  Fed. Rep. of Germany .......... 548/309

Primary Examiner—Henry R. Jiles
Assistant Examiner—Richard A. Schwartz
Attorney, Agent, or Firm—Francis X. Murphy; Charles J. Knuth; Peter C. Richardson

[57] ABSTRACT

A series of amino-and alkylamino-substituted spirohydantoins and pharmaceutically acceptable salts thereof useful as inhibitors of the enzyme aldose reductase and as therapeutic agents for the treatment of chronic complications associated with diabetes are disclosed. Preferred compounds include 6-chloro-8-amino-spiro[4H-2,3-dihydro-1-benzopyran-4,4'-imidazolidine]-2',5'-dione, the 6-fluoro and 8-methylamino- analogs thereof and the corresponding dihydrobenzothiopyran analogs of these compounds. The optical isomers of these compounds having the 4S-configuration are especially preferred.

22 Claims, No Drawings

TREATING DIABETES-ASSOCIATED COMPLICATIONS WITH HYDANTOIN AMINES

BACKGROUND OF THE INVENTION

This invention relates to novel amino- and alkylamino-substituted spirohydantoins and derivatives thereof useful as inhibitors as the enzyme aldose reductase and in the treatment of certain chronic complications arising from diabetes mellitus, such as diabetic cataracts, neuropathy and retinopathy.

In the past various attempts have been made to obtain new antidiabetic agents. Generally these efforts have involved synthesis of new organic compounds, particularly sulfonyl ureas, and determination of their ability to substantially lower blood sugar levels when administered orally. However, little is known about the effect of organic compounds in preventing or alleviating chronic complications of diabetes, such as diabetic cataracts, neuropathy and retinopathy. U.S. Pat. No. 3,821,383 discloses aldose reductase inhibitors like 1,3-dioxo-1H-benz[d,e]-isoquinoline-2(3H)-acetic acid and derivatives thereof to be useful for the treatment of these conditions. More recently, U.S. Pat. Nos. 4,117,230 and 4,130,714 disclose a series of spirohydantoins useful as aldose reductase inhibitors. Such aldose reductase inhibitors function by inhibiting the activity of the enzyme aldose reductase, which is primarily responsible for regulating the reduction of aldoses, such as glucose and galactose to the corresponding polyols, such as sorbitol and galacticol, in humans and other animals. In this way, unwanted accumulations of galacticol in the lens of galactosemic subjects and of sorbitol in the lens, peripheral nervous tissue and kidney of diabetic subjects are prevented or reduced. Accordingly, such compounds are of therapeutic value as aldose reductase inhibitors for controlling certain chronic diabetic complications, especially those of an occular nature, since it is known in the art that the presence of polyols in the lens of the eye leads to cataract formation with a concomittant loss of lens clarity.

SUMMARY OF THE INVENTION

The present invention relates to novel aldose reductase inhibitors useful as therapeutic agents for preventing or alleviating chronic diabetic complications. Specifically, the compounds of the present invention are novel amino- and alkylamino-substituted spirohydantoins of the formula

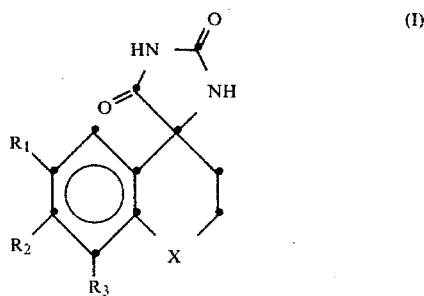

and the pharmaceutically acceptable salts thereof; wherein X is oxygen, sulfur or N-R, wherein R is hydrogen or alkyl of 1 to 3 carbon atoms; $R_1$ is chloro, bromo, fluoro or alkyl of 1 to 3 carbon atoms; one of $R_2$ and $R_3$ is hydrogen; and the other of $R_2$ and $R_3$ is amino, monoalkylamino or dialkylamino, wherein each alkyl group has from 1 to 3 carbon atoms.

One group of compounds of interest is that wherein X is oxygen. Preferably, $R_1$ is chloro or fluoro, $R_2$ is hydrogen and $R_3$ is amino or methylamino. The 4S- isomers of these compounds are preferred.

A further group of compounds of interest is that wherein X is sulfur. Preferably $R_1$ is chloro or fluoro, $R_2$ is hydrogen and $R_3$ is amino or methylamino. The 4S- isomers of these compounds are preferred.

Also embraced by the present invention are pharmaceutical compositions comprising a pharmaceutically acceptable carrier and a compound of formula I in an amount effective for the treatment of diabetes-associated complications, including diabetic cataracts, neuropathy and retinopathy. Preferred compounds for use in such pharmaceutical compositions are those having the preferred substituents for X, $R_1$, $R_2$ and $R_3$ as defined herein above.

The present invention further includes a method of treatment for diabetes-associated complications, including diabetic cataracts, neuropathy and retinopathy, comprising administering to a subject in need of treatment an effective amount of compound of formula I, preferably a compound having the preferred substituents for X, $R_1$, $R_2$ and $R_3$ as defined herein above.

DETAILED DESCRIPTION OF THE INVENTION

The compounds of formula I are readily prepared from starting materials known in the art or prepared by conventional methods. The compounds where $R_3$ is amino are preferably prepared by direct nitration of the corresponding $R_1$-substituted-spirohydantoin i.e. the compound of formula I wherein both $R_2$ and $R_3$ are hydrogen, followed by reduction of the 8-nitro group. The $R_1$-substituted-spirohydantoins are known compounds, see for example U.S. Pat. No. 4,117,230 and 4,130,714. The nitration is generally effected by reaction of the $R_1$-substituted-spirohydantoin with nitric acid at a temperature from about 20° to 150° C., preferably from about 50° to 125° C. The reaction is conducted in an organic solvent such as an anhydrous carboxylic acid of 1 to 4 carbon atoms, preferably glacial acetic acid, or in the corresponding carboxylic acid anhydride, or in an acid such as concentrated sulfuric acid, concentrated hydrochloric acid and the like. The resulting 8-nitro-substituted compound of formula I (i.e. where $R_3$ is nitro) is then reduced to the corresponding amino compound using conventional reducing agents known in the art for effecting the reduction of a nitro group. For example, the reduction may conveniently be effected by the use of iron powder in the presence of an acid such as hydrochloric acid or the like, generally in aqueous solution at a temperature of about 50° C. to about 150° C., preferably from about 75° C. to 125° C. The reduction may also be effected by catalytic hydrogenation, for example using platinum, palladium or nickel catalyst and gaseous hydrogen, or by the use of sodium amalgam and the like.

The compounds of formula I where $R_3$ is amino may also be prepared from appropriately substituted ketones of the formula

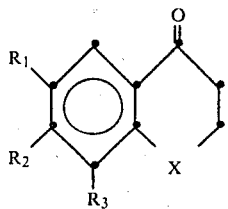

wherein $R_2$ and $R_3$ are each hydrogen. The compound of formula II is nitrated under the conditions described above to form the corresponding 8-nitro compound. The nitro group is then reduced, preferably using iron powder in the presence of acid, preferably hydrochloric acid, under the conditions described above. The resulting 8-amino ketone is then condensed with an alkali metal cyanide, such as sodium or potassium cyanide and ammonium carbonate to form the desired spirohydantoin of formula I wherein $R_3$ is amino. The condensation reaction is generally conducted in an organic solvent, such as dioxane, tetrahydrofuran, ethylene glycol, alcohols of 1 to 6 carbon atoms and the like at a temperature from about 50° C. to 150° C., preferably from about 90° C. to 125° C.

Alternatively, the 8-nitro substituted ketone of formula II formed as described above may be condensed with the alkali metal cyanide and ammonium carbonate as described to form the compound of formula I wherein $R_3$ is nitro. This 8-nitro group is then reduced to amino, as previously described.

The 8-nitro ketones i.e. the compounds of formula II wherein $R_3$ is nitro, can also be obtained from appropriately substituted 2-nitro-4-$R_1$-substituted phenols, thiophenols or anilines, to prepared compounds wherein X is oxygen, sulfur or nitrogen, respectively. The ketones are then formed by methods known in the art, for example as described in J. Organic Chemistry, 28, 1135 (1963) and in U.S. Pat. No. 4,117,230. The 8-nitro compound of formula II is then converted to the corresponding compound of formula I wherein $R_3$ is amino, as previously described i.e. by reduction of the 8-nitro group followed by condensation of the ketone with an alkali metal cyanide and ammonium carbonate, or by first effecting the condensation followed by reduction of the 8-nitro group.

Compounds of formula I wherein $R_2$ is amino and $R_3$ is hydrogen are formed from the appropriate 7-nitro ketones of formula II i.e. wherein $R_2$ is nitro and $R_3$ is hydrogen, by the methods previously described. These ketones are prepared from the corresponding 3-nitro-4-$R_1$-substituted phenols, thiophenols or anilines, as previously described.

The compounds of formula I wherein one of $R_2$ and $R_3$ is alkylamino are readily formed from the corresponding compounds of formula I where the appropriate $R_2$ or $R_3$ substituent is amino by reaction with an appropriate alkyl halide. Reaction with about 1 mole of alkyl halide is employed to form the compounds wherein one of $R_2$ or $R_3$ is monoalkylamino. By reaction with a further mole of alkyl halide, having either the same or different alkyl group therein, the corresponding dialkylamino-substituted compounds may be formed. The alkylamino analogs may also be prepared by the reaction of the corresponding amino compound with an appropriate acyl halide, followed by reduction of the carbonyl group of the acyl radical. Thus, for example, compounds of formula I wherein $R_2$ or $R_3$ is ethylamino may be prepared by reacting the corresponding compound wherein $R_2$ or $R_3$ is amino with an acetyl halide, such as acetyl chloride, followed by reduction of the carbonyl group of the acetyl radical, for example using lithium aluminum hydride, sodium borohydride, catalytic hydrogenation and the like. Corresponding dialkylamino-substituted compounds can then be formed by reaction with an appropriate alkyl halide.

It will be understood that the compounds of formula I contain an assymetric carbon atoms and that these compounds will exhibit optical isomerism. Preferred compounds of this invention are those of formula I having the 4S-configuration, i.e. the compounds of the formula

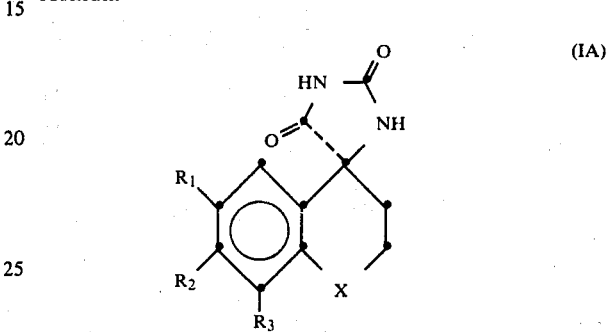

It is to be understood that both the optical isomers and racemic mixtures thereof are within the scope of the specification and the claims thereof.

The optically active compounds of formula IA wherein $R_3$ is amino or alkylamino may be prepared by nitration and reduction of the corresponding optically active spirohydantoin i.e. a compound of formula IA wherein $R_2$ and $R_3$ are each hydrogen by the methods described previously. Further, the optically active compounds of formula IA wherein either $R_2$ or $R_3$ is amino or alkylamino may be prepared by resolution of the racemic mixture of compounds of formula I, formed by the methods described above, using resolution methods well known in the art. The optically active isomers may be obtained by reacting the racemic compounds of formula I with an optically active organic acid, such as tartaric acid or the like, to form an acid addition salt. Alternatively, the racemic compound of formula I may be complexed with an optically active base, such as an alkaloid, for example brucine or cinchonidine. The diastereoisomeric salts or adducts formed from the reaction of the racemic compound of formula I with the optically active acid or base, as described above, may then be separated, for example by fractional crystallization or the like, and converted to the desired optically active isomer by decomposition of the salt or adduct by addition of base or acid, as appropriate.

This invention also embraces the pharmaceutically acceptable salts of the compounds of formula I. Because of the presence of the 7- or 8-amino or alkylamino group, acid addition salts of these compounds are readily prepared using methods known in the art. For example, such salts may be prepared by contacting the free base with the appropriate mineral or organic acid in either aqueous solution or in a suitable organic solvent. The solid salt may then be obtained by precipitation or by evaporation of the solvent. The pharmaceutically acceptable acid addition salts of this invention include, but are not limited to, the hydrochloride, hydrobromide, hydroiodide, sulfate, bisulfate, nitrate, phosphate, acetate, lactate, maleate, fumarate, citrate, tartrate, succinate, gluconate, and the like. Preferred salts are the hydrochloride, hydroiodide and hydrobromide.

Alternatively, because of the acidic hydrogen atom in the hydantoin ring of the compounds of formula I, salts may be formed with pharmaceutically acceptable cations by conventional methods. Thus, these salts may be readily prepared by treating the compound of formula I with an aqueous solution of the desired pharmaceutically acceptable cation and evaporating the resulting solution to dryness, preferably under reduced pressure. Alternatively, a lower alkyl alcohol solution of the compound of formula I may be mixed with an alkoxide of the desired metal and subsequently evaporating the solution to dryness. Suitable pharmaceutically acceptable cations for this purpose include, but are not limited to potassium, sodium, ammonium, calcium and magnesium.

It is to be understood that by use of the term pharmaceutically acceptable salts in the disclosure and claims hereof it is meant to embrace both the acid addition salts and the salts formed with appropriate cations, as described above.

The novel compounds of formula I and the pharmaceutically acceptable salts thereof are useful as inhibitors of the enzyme aldose reductase in the treatment of chronic complications of diabetes, such as diabetic cataracts, retinopathy and neuropathy. As used in the claims and specification hereof, treatment is meant to include both the prevention or alleviation of such conditions. The compound may be administered to a subject in need of treatment by a variety of conventional routes of administration, including orally, parenterally and topically. In general, these compounds will be administered orally or parenterally at dosages between about 0.05 and 25 mg./kg. body weight of the subject to be treated per day, preferably from about 0.1 to 10 mg./kg. However, some variation in dosage will necessarily occur depending on the condition of the subject being treated and the person responsible for administration will, in any event, determine the appropriate dose for the invidual subject.

The novel compound of the invention may be administered alone or in combination with pharmaceutically acceptable carriers, in either single or multiple doses. Suitable pharmaceutical carriers include inert solid diluents or fillers, sterile aqueous solution and various organic solvents. The pharmaceutical compositions formed by combining the novel compounds of formula I and the pharmaceutically acceptable carriers are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene, glycol, glycerin and combinations thereof.

For parenteral administration, solutions of the novel compound of formula I in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

The higher solubility of the present compounds of formula I and of the pharmaceutically acceptable salts thereof in aqueous solution, compared to other similar compounds and especially compared to the corresponding compounds of formula I having no amino or alkylamino amino substituents, is advantageous not only for the preparation of aqueous pharmaceutical compositions for parenteral administration, as described above, but more particularly for the preparation of pharmaceutical compositions suitable for use as ophthalmic solutions. Such ophthalmic solutions are of principal interest for the treatment of diabetic cataracts by topical administration and the treatment of such conditions in this manner is a preferred embodiment of the present invention. Thus, for the treatment of diabetic cataracts the compounds of this invention are administered to the eye of the subject in need of treatment in the form of an ophthalmic preparation prepared in accordance with conventional pharmaceutical practice, see for example "Remington's Pharmaceutical Sciences" 15th Edition, pages 1488 to 1501 (Mack Publishing Co., Easton, Pa.). The ophthalmic preparation will contain a compound of formula I or a pharmaceutically acceptable salt thereof in a concentration from about 0.1 to about 5% by weight, preferably from about 0.5 to about 2% in a pharmaceutically acceptable solution, suspension or ointment. Some variation in concentration will necessarily occur, depending on the particular compound employed, the condition of the subject to be treated and the like, and the person responsible for treatment will determine the most suitable concentration for the individual subject. The ophthalmic preparation will preferably be in the form of a sterile aqueous solution containing, if desired, additional ingredients, for example preservatives, buffers, tonicity agents, antioxidants and stabilizers, nonionic wetting or clarifying agents, viscosity-increasing agents and the like. Suitable preservatives include benzalkonium chloride, benzethonium chloride, chlorobutanol, thimerosal and the like. Suitable buffers include boric acid, sodium and potassium bicarbonate, sodium and potasssium borate, sodium and potassium carbonate, sodium acetate, sodium biphosphate and the like, in amounts sufficient to maintain the pH at between about 6 and 8, preferably between about 7 and 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%. Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxymethylpropylcellulose, lanolin, methylcellulose, petrolatum, polyethylene glycol, polyvinyl alcohol, polyvinylpyrrolidone, carboxymethylcellulose and the like. The ophthalmic preparation will be administered topically to the eye of the subject in need of treatment by conventional methods, for example in the form of drops or by bathing the eye in the ophthalmic solution.

The activity of the compounds of the present invention as agents for the control of chronic diabetic complications may be determined by a number of standard biological or pharmacological tests. Suitable tests include (1) measuring their ability to inhibit the enzyme activity of isolated aldose reductase; (2) measuring their ability to reduce or inhibit sorbitol accumulation in the sciatic nerve of acutely streptozotocinized, i.e. diabetic rats; (3) measuring their ability to reverse already-elevated sorbitol levels in the sciatic nerve and lens of chronic streptozotocin-induced diabetic rats; (4) measuring their ability to prevent or inhibit galacticol formation in the lens of acutely galactosemic rats; and (5) measuring their ability to delay cataract formation and reduce the severity of lens opacities in chronic galactosemic rats.

The present invention is illustrated by the following examples. It will be understood, however, that the invention is not limited to the specific details of these examples. In these examples, all temperatures are in degrees centigrade.

EXAMPLE 1

6-Chloro-8-nitro-spiro[4H-2,3-dihydro-1-benzopyran-4,4'-imidazolidine]-2',5'-dione A solution of 3.80 g (0.015 mol) of 6-chlorospiro[4H-2,3-dihydro-1-benzopyran-4,4'-imidazolidine]-2',5'-dione (U.S. Pat. No. 4,117,230) in 40 ml of acetic anhydride was treated with 0.64 ml of concentrated nitric acid at ambient temperature for 18 hours. The mixture was poured into 300 ml of water, stirred for 4 hours and filtered. The solid was recrystallized from ethanol-diethyl ether to give 0.78 g of the N-acetyl derivative of the title compound (m/e 339). The mother liquor was concentrated to a residue which was crystallized from methanol to give the title compound; 0.48 g m.p. 201°–203° C.

EXAMPLE 2

8-Amino-6-chloro-spiro[4H-2,3-dihydro-1-benzopyran-4,4'-imidazolidine]-2',5'-dione hydrochloride The compound of Example 1 (100 mg, 0.34 mmol) was reacted with 120 mg (2.15 mmol) of iron powder and seven drops of concentrated hydrochloric acid in 3 ml of water at 100° C. for 2 hours. The cooled reaction mixture was neutralized with sodium carbonate and extracted with 2×100 ml ether. The organic phase was dried over magnesium sulfate, filtered, and evaporated in vacuo to a residue which was redissolved in 100 of ether and perfused with hydrogen chloride gas. The volatiles were distilled in vacuo and the solid residue was recrystallized from methanol/ether; 75 mg (83%) m.p. 180°–182° C. (d)

EXAMPLE 3

4S-6-Fluoro-8-nitro-spiro[4H-2,3-dihydro-1-benzopyran-4,4'-imidazolidine]-2',5'-dione A solution of 10.00 g (0.0423 mol) of 4S-6-fluorospiro[4H-2,3-dihydro-1-benzopyran-4,4'-imidazolidine]-2',5'-dione (U.S. Pat. No. 4,130,714 in 50 ml of glacial acetic acid was treated with 13.5 ml of concentrated nitric acid and heated at 105° C. for 4 hours. The reaction mixture was concentrated in vacuo to a residue which was dissolved in 200 ml of ethyl acetate and washed with 2×100 ml brine, 2×100 ml saturated sodium bicarbonate and 100 ml brine, decolorized with activated carbon (Darco), dried over magnesium sulfate, filtered and evaporated to a foam which was recrystallized from water; 4.60 g (39%), mp 130° C.

EXAMPLE 4

4S-8-amino-6-fluoro-spiro[4H-2,3-dihydro-1-benzopyran-4,4'-imidazolidine]-2',5'-dione hydrochloride The compound of Example 3 (4.50 g, 0.0160 mol) was reacted with 5.40 g (0.0966 mol) of iron powder and 2.25 ml (0.027 mol) of concentrated hydrochloric acid in 150 ml of water at 100° C. for 1 hour. The cooled reaction mixture was partitioned between 100 ml of saturated sodium bicarbonate and 200 ml of ethyl acetate. The basic phase was extracted with 100 ml ethyl acetate. The combined organic phases were washed with 100 ml of brine, dried over magnesium sulfate, filtered and evaporated in vacuo to a powder. This was dissolved in methanol, perfused with hydrochloric acid gas and evaporated in vacuo to a powder which was recrystallized from acetonitrile; 1.25 g (27%) m.p. 201° C. (d).

EXAMPLE 5

4S-8-amino-6-fluoro-spiro[4H-2,3-dihydro-1-benzothiopyran-4,4'-imidazolidine]-2',5'-dione hydrochloride The title compound is prepared in two steps using the methods of Examples 3 and 4 from 4S-6-fluoro-spiro[4H-2,3-dihydro-1-benzothiopyran-4,4'-imidazolidine]-2',5'-dione (U.S. Pat. No. 4,130,714).

EXAMPLE 6

8-Amino-6-chloro-spiro[4H-2,3-dihydro-1-benzothiopyran-4,4'-imidazolidine]-2',5'-dione hydrochloride The title compound is prepared in two steps using the methods of Examples 3 and 4 from 6-chloro-spiro[4H-2,3-dihydro-1-benzothipyran-4,4'-imidazolidine]-2',5'-dione (U.S. Pat. No. 4,117,230).

EXAMPLE 7

8'-Amino-6'-chloro-1',2',3',4'-tetrahydro-spiro[imidazolidine-4,4'-quinoline]-2,5-dione hydrochloride The title compound is prepared in two steps using the methods of Examples 3 and 4 from 6-chloro-1',2',3',4'-tetrahydro-spiro[imidazolidine-4,4'-quinoline]-2,5-dione.

The starting material is obtained by the reaction of 6-chloro-2,3-dihydro-4(1H)-quinolone, which is prepared by the procedure described in J. Organic Chemistry, 28, 1135 (1963), with potassium cyanide and ammonium carbonate in 50% aqueous ethanol at 120° C.

EXAMPLE 8

4S-8-Acetylamino-6-fluoro-spiro[4H-2,3-dihydro-1-benzoyran-4,4'-imidazolidine]-2',5'-dione The title compound is prepared from the compound of Example 4 and acetyl chloride in pyridine according to the method of Bradshaw (J. Org. Chem. 35, 1219 [1970]). The reaction mixture is concentrated in vacuo to a residue which is dissolved in ethyl acetate and washed with sodium bicarbonate solution and dilute hydrochloric acid solution, dried over magnesium sulfate and evaporated in vacuo to a residue which is crystallized.

The title compound is converted to 4S-ethylamino-6-fluoro-spiro[4H-2,3-dihydro-1-benzopyran-4,4'-imidazolidine]-2',5'-dione by reduction with lithium aluminum hydride in ether at 20° C.

EXAMPLE 9

4S-8-Methylamino-6-fluoro-spiro[4H-2,3-dihydro-1-benzopyran-4,4'-imidazolidine]-2,5'-dione The title compound is prepared from the compound of Example 4 and methyl iodide by treatment with potassium hydroxide according to the method of Young (J. Amer. Chem. Soc., 82 6163 (1970). The reaction mixture is evaporated in vacuo to a residue which is taken up in ethyl acetate and washed with sodium bicarbonate solution and brine, dried over magnesium sulfate, concentrated to a residue and crystallized.

EXAMPLE 10

The compounds of Example 2 and 4 were tested for their ability to reduce or inhibit aldose reductase enzyme activity, following the procedure described in U.S. Pat. No. 3,821,383 and based on the procedure of Hayman et. al., Journal of Biological Chemistry, 240 877 (1965). The substrate employed was partially purified aldose reductase enzyme obtained from human placenta. The results obtained with each compound at a concentration of $10^{-6}$ M are expressed as percent inhibition of enzyme activity.

| Compound of | % Inhibition at $10^{-6}$M |
| --- | --- |
| Example 2 | 58 |
| Example 4 | 40 |

EXAMPLE 11

The compounds of Example 2 and 4 were tested for their ability to reduce or inhibit sorbitol accumulation in the sciatic nerve of streptozotocinized (i.e. diabetic) rats by the procedure essentially described in U.S. Pat. No. 3,821,383. In the present study, the amount of sorbitol accumulation in the sciatic nerves was measured 27 hours after induction of diabetes. The compounds were administered orally at the dose levels of 0.25 mg/kg at 4, 8 and 24 hours following the administration of streptozotocin. The results obtained in this manner are presented below in terms of percent inhibition (%) afforded by the test compound as compared to the case where no compound was administered (i.e. the untreated animal, where sorbitol levels normally rise from approximately 50-100 mM/g. tissue to as high as 400 mM/g. tissue in the 27 hour test period):

| Compound of | % Inhibition at 0.25 mg/kg |
| --- | --- |
| Example 2 | 17 |
| Example 4 | 40 |

We claim:
1. A compound of the formula

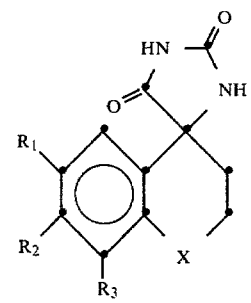

or a the pharmaceutically acceptable salt thereof; wherein X is oxygen, sulfur or >N—R, wherein
  R is hydrogen or alkyl of 1 to 3 carbon atoms;
  $R_1$ is chloro, bromo, fluoro or alkyl of 1 to 3 carbon atoms;
  one of $R_2$ and $R_3$ is hydrogen; and the other of $R_2$ and $R_3$ is amino, monoalkylamino or dialkylamino, wherein each alkyl group has from 1 to 3 carbon atoms.

2. A compound of claim 1 wherein X is oxygen.
3. A compound of claim 2 wherein $R_2$ is hydrogen and $R_3$ is amino or methylamino.
4. A compound of claim 3 wherein $R_1$ is chloro and $R_3$ is amino.
5. A compound of claim 3 wherein $R_1$ is chloro and $R_3$ is methylamino.
6. A compound of claim 3 wherein $R_1$ is fluoro and $R_3$ is amino.
7. A compound of claim 3 wherein $R_1$ is fluoro and $R_3$ is methylamino.
8. A compound of claim 4, 5, 6 or 7 wherein the compound is the 4S-isomer.
9. A compound of claim 1 wherein X is sulfur.
10. A compound of claim 9 wherein $R_2$ is hydrogen and $R_3$ is amino or methylamino.
11. A compound of claim 10 wherein $R_1$ is chloro and $R_3$ is amino.
12. A compound of claim 10 wherein $R_1$ is chloro and $R_3$ is methylamino.
13. A compound of claim 10 wherein $R_1$ is fluoro and $R_3$ is amino.
14. A compound of claim 10 wherein $R_1$ is fluoro and $R_3$ is methylamino.
15. A pharmaceutical composition comprising a pharmaceutically acceptable carrier and a compound of claim 1 in an amount effective for the treatment of diabetes-associated complications.
16. A pharmaceutical composition of claim 15 wherein X is oxygen.
17. A pharmaceutical composition of claim 16 wherein $R_1$ is chloro or fluoro, $R_2$ is hydrogen and $R_3$ is amino or methylamino.
18. A pharmaceutical composition of claim 17 wherein the compound is the 4S-isomer.
19. A method of treating diabetes-associated complications which comprises administering to a diabetic subject an effective amount of a compound of claim 1.
20. A method of claim 19 wherein X is oxygen.
21. A method of claim 20 wherein $R_1$ is chloro or fluoro, $R_2$ is hydrogen and $R_3$ is amino or methylamino.
22. A method of claim 21 wherein the compound is the 4S-isomer.

* * * * *